(12) United States Patent
Hirama

(10) Patent No.: US 7,951,084 B2
(45) Date of Patent: May 31, 2011

(54) ULTRASONIC DIAGNOSTIC APPARATUS AND ULTRASONIC DIAGNOSTIC METHOD

(75) Inventor: Makoto Hirama, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 1596 days.

(21) Appl. No.: 11/205,156

(22) Filed: Aug. 17, 2005

(65) Prior Publication Data
US 2006/0058661 A1   Mar. 16, 2006

(30) Foreign Application Priority Data
Aug. 18, 2004   (JP) .................. 2004-238607

(51) Int. Cl.
   *A61B 8/00*   (2006.01)
(52) U.S. Cl. ........................ 600/443; 600/437
(58) Field of Classification Search .......... 600/441–445, 600/437, 481, 447; 601/1–4; 73/625, 629, 73/602, 606, 622, 454; 347/235
See application file for complete search history.

(56) References Cited

U.S. PATENT DOCUMENTS

| | | | |
|---|---|---|---|
| 5,129,399 A | | 7/1992 | Hirama |
| 5,331,855 A | * | 7/1994 | Takashita et al. ................ 73/602 |
| 5,515,849 A | * | 5/1996 | Murashita et al. ............. 600/479 |
| 5,664,572 A | * | 9/1997 | Kishimoto ..................... 600/443 |
| 5,841,889 A | * | 11/1998 | Seyed-Bolorforosh ....... 382/128 |
| 6,126,598 A | | 10/2000 | Entrekin et al. |
| 2003/0097068 A1 | * | 5/2003 | Hossack et al. ............... 600/443 |
| 2004/0254462 A1 | * | 12/2004 | Kawagishi et al. ........... 600/437 |

FOREIGN PATENT DOCUMENTS

| | | |
|---|---|---|
| JP | 62-72340 | 4/1987 |
| JP | 3-99651 | 4/1991 |

* cited by examiner

*Primary Examiner* — Unsu Jung
*Assistant Examiner* — Lawrence N Laryea
(74) *Attorney, Agent, or Firm* — Oblon, Spivak, McClelland, Maier & Neustadt, L.L.P.

(57) ABSTRACT

An ultrasonic diagnostic apparatus comprising an ultrasonic transmitting unit, an image signal generating unit and a signal addition unit. The ultrasonic transmitting unit transmits an ultrasonic wave having a wave surface except a plane wave surface and a focused focal wave surface to a subject so that shapes of wave surface portions change mutually in time on a same scanning line. The image signal generating unit receives reflected waves produced by the wave surface portions and generating image signals according to the reflected waves received. The signal addition unit obtains an image signal of which a speckle noise is reduced by adding the image signals mutually.

19 Claims, 10 Drawing Sheets

ULTRASONIC DIAGNOSTIC APPARATUS AND ULTRASONIC DIAGNOSTIC METHOD

BACKGROUND OF THE INVENTION

1. Field of the Invention

The present invention relates to an ultrasonic diagnostic apparatus and an ultrasonic diagnostic method which generate image signals by transmitting and receiving ultrasonic waves to an internal portion of a subject, and more particularly, to an ultrasonic diagnostic apparatus and an ultrasonic diagnostic method which make it possible to reduce an effect of speckle noise generated on occurrence of mutual phase interference between scattering waves produced with a scattering object within the subject.

2. Description of the Related Art

In the ultrasonic diagnostic apparatus, electric pulses are impressed on respective ultrasonic minute oscillating elements in an ultrasonic probe with delay times different from one ultrasonic minute oscillating element to another, and the obtained transmission beam is applied to the inside of a subject. Then, reflected waves from the subject are received by the same ultrasonic minute oscillating element group that has applied the transmission beam, and a reception beam is formed by performing amplification/delay-addition. Furthermore, radio frequency (RF) signal obtained from the reception beam is detected/compressed to acquire an image signal. In particular, the electronic scanning ultrasonic diagnostic apparatus obtains an image inside the subject by electronically scanning the subject with this ultrasonic beam.

FIG. 10 is a block diagram of a conventional ultrasonic diagnostic apparatus.

In a conventional ultrasonic diagnostic apparatus 1, a focus wave surface generator 2 generates a plurality of mutually different pieces of delay time information corresponding to respective members of a ultrasonic minute oscillating element group in an ultrasonic probe 3, and provides the generated information to a pulsar controller 4. The pulsar controller 4 generates a control signal such that a pulsar group 5 generates electric pulses in response to respective pieces of delay time information, and provides the generated control signal to the pulsar group 5.

Then, based on the control signal received from the pulsar controller 4, the pulsar group 5 generates electric pulses, and the generated electric pulses are impressed to the ultrasonic minute oscillating element group in the ultrasonic probe 3, with delay times different from one minute oscillating element to another. As a result, ultrasonic waves are transmitted to a subject (not shown) from the ultrasonic minute oscillating element group in the ultrasonic probe 3, with delay times different from one minute oscillating element to another, and thereby a transmission focus is obtained. Thus, a transmission beam of the ultrasonic waves is formed inside the subject.

Furthermore, reflected waves generated inside the subject are received by the same ultrasonic minute oscillating element group in the ultrasonic probe 3, and are provided to a preamplifier group 6. The preamplifier group 6 amplifies the reflected wave signals received from the ultrasonic minute oscillating element group, and provides the reflected wave signals amplified to a delay circuit group 7. The delay circuit group 7 performs a delay addition of the reflected wave signals, thereby forming a reception beam of the reflected waves. Thus, a scanning line RF signal of the reflection waves is generated in the delay circuit group 7.

Next, the scanning line RF signal generated in the delay circuit group 7 is provided to an image signal detecting unit 8, and the image signal detecting unit 8 detects/compresses the scanning line RF signal to obtain an image signal. The image signal obtained by the image signal detecting unit 8 is given to an image display circuit 9. The image display circuit 9 converts the image signal received from the image signal detecting unit 8 into a luminance signal of an image mapped in accordance with the signal intensities, and gives the luminance signal to a monitor 10. As a consequence, on the monitor 10, an image inside the subject is displayed by luminance in accordance with the signal intensities of the image signal.

On the other hand, a part to be diagnosed inside the subject, e.g., an organ such as the liver parenchyma has structures minute relative to the width of an ultrasonic wave beam to be applied. This is a situation equivalent to one where an infinite number of scattering objects exists in an irradiation region of ultrasonic waves. Once a region having such a minute structures has been irradiated with ultrasonic waves, scattering waves generate from a large number of respective scattering objects, and the scattering waves generated cause a phase interference with one another, thereby incurring so-called "speckle noise".

This type of speckle noise is similar to speckle noise occurring when laser beams are passed through the atmosphere with fluctuation, and it is attributed to a phase interference among wave surfaces. Typically, the speckle noise comprises speckles each having a size equivalent to that corresponding to the resolution of an ultrasonic diagnostic apparatus, and the average intensity thereof is proportional to the scattering intensity of minute scattering objects. The shapes themselves of the speckles of the speckle noise are not representative of the structure of an organ of the subject. The problem is that the speckle noise impairs the visibility of minute structures inside the subject or the difference in minute scattering intensity.

With such being the situation, in recent years, to reduce the influence of the speckle noise, a so-called "spatial compound" method has been implemented, in which ultrasonic waves are transmitted/received with respect the subject from a plurality of directions, and in which a plurality of images obtained by reflected waves from respective directions are added to one another. (see, for example, Japanese Patent Application (Laid-Open) No. 62-72340 and Japanese Patent Application (Laid-Open) No. 3-99561).

FIG. 11 is a diagram showing an example of wave surface of ultrasonic wave which is to be transmitted to a subject in a perpendicular direction in the case that an image is generated with the conventional spatial compound technology. FIG. 12 is a diagram showing an example of wave surface of ultrasonic wave which is to be transmitted to a subject in the direction of oblique in the case that an image is generated with the conventional spatial compound technology.

Here, for the sake of simplification, suppose that, when an ultrasonic wave is perpendicularly transmitted to the subject, four scattering objects having the same size exist evenly spaced in the different depths Z, and at random position in the direction X perpendicular to the depth direction of the ultrasonic wave.

As shown in FIG. 11, usually, an ultrasonic wave is transmitted so that the wave surface of a plane wave becomes perpendicular to the transmitting/receiving surface direction X of the ultrasonic probe, and scattering waves are caused by the scattering objects existing inside the subject. Moreover, as shown in FIG. 12, to reduce the influence of speckle noise, another ultrasonic wave which is a plane wave is transmitted from an oblique direction Z' so that it's wave surface tilts with respect to the transmitting/receiving surface direction X of the ultrasonic probe, and scattering waves are caused by the scattering objects existing inside the subject.

In this manner, when ultrasonic waves are transmitted from mutually different directions, scattering waves in response to directions of transmitted ultrasonic waves occur.

FIG. 13 is a diagram showing waveform of the scattering wave produced with the scattering object when the ultrasonic wave is transmitted so that the wave surface of the plane wave becomes vertical to the direction X of the transmission-and-reception face of the ultrasonic probe as shown in FIG. 11. FIG. 14 is a diagram showing waveform of the scattering wave produced with the scattering object when the ultrasonic wave is transmitted so that the wave surface of the plane wave inclines to the direction X of the transmission-and-reception face of the ultrasonic probe as shown in FIG. 12.

As shown in FIG. 13, when an ultrasonic wave is perpendicularly transmitted to the subject, since the four scattering objects exist evenly spaced in the mutually different depths Z, four scattering waves each having a similar waveform occur at regular intervals in correspondence with the ultrasonic wave penetration depths. On the other hand, as shown in FIG. 14, transmitting an ultrasonic wave to the subject in the oblique direction Z' results in that the four scattering objects exist unevenly spaced at the positions where penetration depths Z' of the ultrasonic wave are different each other, since the four scattering objects exist at random in the transmitting/receiving surface direction X of the ultrasonic probe. Consequently, four scattering waves having a similar waveform occur at irregular intervals in correspondence with the ultrasonic wave penetration depths Z'.

As a result, obtained are scattering waves (speckle noise) having interference patterns mutually different in accordance with the directions of the transmitted ultrasonic waves.

FIG. 15 is a diagram showing the result of interference on the scattering waves shown in FIG. 13. FIG. 16 is a diagram showing the result of interference on the scattering waves shown in FIG. 14.

As shown in FIG. 15, when an ultrasonic waves is perpendicularly transmitted to the subject, scattering waves that are evenly spaced occur, and they interference with one another, resulting in a regular waveform. On the other hand, as shown in FIG. 16, when an ultrasonic wave is obliquely transmitted to the subject, scattering waves that are unevenly spaced occur, and they interference with one another, resulting in an irregular waveform.

That is, even if the positioning of scattering objects is the same, provided that directions of the wave surfaces of transmitted ultrasonic waves are different, the combination of scattering objects causing scattering changes, and thereby speckle noise based on different phase interferences is obtained. Then, images obtained by thus changing the direction of ultrasonic wave beams are added, so that the reduction in speckle noise, namely, the stabilization of fluctuation is performed statistically by averaging independent images.

FIG. 17 is a diagram showing an example of scanning direction by the ultrasonic wave in case that an image is generated with the conventional spatial compound technology. FIG. 18 is a conceptual diagram explaining the way of generating images with spatial compounding using data obtained by scanning in the scanning direction shown in FIG. 17.

As shown in FIG. 17, for example, when scanning is performed in three different directions, three scattering waves with mutually different interference patterns are obtained. Then, as shown in FIG. 18, three scattering waves obtained from the identical position are added. This allows the reduction in speckle noise.

However, the generation of an ultrasonic diagnostic image by the conventional spatial compound technique involves the following problems.

First, the spatial compound is a technique for obtaining a single image by adding a plurality of images obtained by transmitting/receiving ultrasonic waves with respect to a plurality of directions. However, in order to obtain a speckle reducing effect, the independence of a speckle pattern in an image to undergo addition is required. For this purpose, it is necessary that the angles formed between directions of transmissions/receptions of ultrasonic waves performed over a plurality of times be large to an extent such as to secure the independence of speckle pattern. However, since the aperture of the ultrasonic probe is limited, the number of independent images obtainable is restricted. This causes a problem in that a sufficient speckle reducing effect may be unattainable.

Secondly, with an ultrasonic wave transmitted/received, when the transmission/reception direction is tilted with respect to the transmitting/receiving surface of the ultrasonic probe, it is necessary to perform scanning at an angle larger than the angle of view at which display is practically performed, for image addition. This raises a problem in that the number of frames that can be imaged per acquired data or per unit time decreases. Specifically, when a region filled with dotted lines in FIG. 17 is a display region necessary to be displayed as an image, if the transmission/reception direction of ultrasonic waves is perpendicular to the transmitting/receiving surface of the ultrasonic probe, it suffices to scan the display region alone. However, when the transmission/reception direction of ultrasonic waves is tilted with respect to the transmitting/receiving surface of the ultrasonic probe, it is necessary to scan a region outside the display region.

Conversely, when the transmission/reception direction of ultrasonic waves is tilted with respect to transmitting/receiving surface of the ultrasonic probe, if the display region alone is scanned, there occur portions subjected to no scanning so that the speckle reducing effect varies from one spot of the image to another, resulting in unevenness of the image. Specifically, as shown in FIG. 17, when the display region alone is scanned from three directions, i.e., from the front and right-and-left oblique directions, a speckle reducing effect is obtained with respect to a region where the three scanning lines are intersected, whereas with respect to a region where these scanning lines are not intersected, no speckle reducing effect can be obtained.

A third problem is that, in order to obtain the image of a single point, transmitting/receiving operations of an ultrasonic wave over a plurality of times are required, thereby deteriorating real time characteristic. As shown in FIG. 17, when scanning the display region alone from three directions, i.e., the front and right-and-left oblique directions, three transmitting/receiving operations are needed to obtain the image of a single point.

SUMMARY OF THE INVENTION

Accordingly, the present invention has been made in light of the conventional situations, and it is an object of the present invention to provide an ultrasonic diagnostic apparatus and an ultrasonic diagnostic method which make it possible to reduce an effect of speckle noise generated on occurrence of mutual phase interference between scattering waves produced with a scattering object within the subject adequately and efficiently.

Furthermore, it is another object of the present invention to provide an ultrasonic diagnostic apparatus and an ultrasonic diagnostic method which make it possible to reduce speckle noise generated with a scattering object within the subject with improving deterioration of observability in real-time.

In an aspect, to achieve the object, the present invention provides an ultrasonic diagnostic apparatus comprising: an ultrasonic transmitting unit for transmitting an ultrasonic wave having a wave surface except a plane wave surface and a focused focal wave surface to a subject so that shapes of wave surface portions change mutually in time on a same scanning line; an image signal generating unit for receiving reflected waves produced by the wave surface portions and generating image signals according to the reflected waves received; and a signal addition unit for obtaining an image signal of which a speckle noise is reduced by adding the image signals mutually.

Furthermore, the ultrasonic transmitting unit can be configured to transmit the ultrasonic wave to the subject so that phases of the wave surface portions change mutually in time and each shape of the wave surface portions changes in time respectively.

Furthermore, in an aspect, to achieve the object, the present invention provides an ultrasonic diagnostic apparatus comprising: an ultrasonic transmitting unit for transmitting an ultrasonic wave of which a phase value varies according to a portion on a wave surface to a subject so that shapes of wave surface portions change mutually in time on a same scanning line; an image signal generating unit for receiving reflected waves produced by the wave surface portions and generating image signals according to the reflected waves received; and a signal addition unit for obtaining an image signal of which a speckle noise is reduced by adding the image signals mutually.

Furthermore, in an aspect, to achieve the object, the present invention provides an ultrasonic diagnostic method comprising steps of: transmitting unit for transmitting an ultrasonic wave having a wave surface except a plane wave surface and a focused focal wave surface to a subject so that shapes of wave surface portions change mutually in time on a same scanning line; receiving reflected waves produced by the wave surface portions and generating image signals according to the reflected waves received; and obtaining an image signal of which a speckle noise is reduced by adding the image signals mutually.

With the ultrasonic diagnostic apparatus and the ultrasonic diagnostic method as described above, it is possible to reduce an effect of speckle noise generated on occurrence of mutual phase interference between scattering waves produced with a scattering object within the subject adequately and efficiently.

Furthermore, it is possible to reduce speckle noise generated with a scattering object within the subject with improving deterioration of observability in real-time.

DESCRIPTION OF THE PREFERRED EMBODIMENTS

An ultrasonic diagnostic apparatus and an ultrasonic diagnostic method according to embodiments of the present invention will be described with reference to the accompanying drawings.

Figure 1:
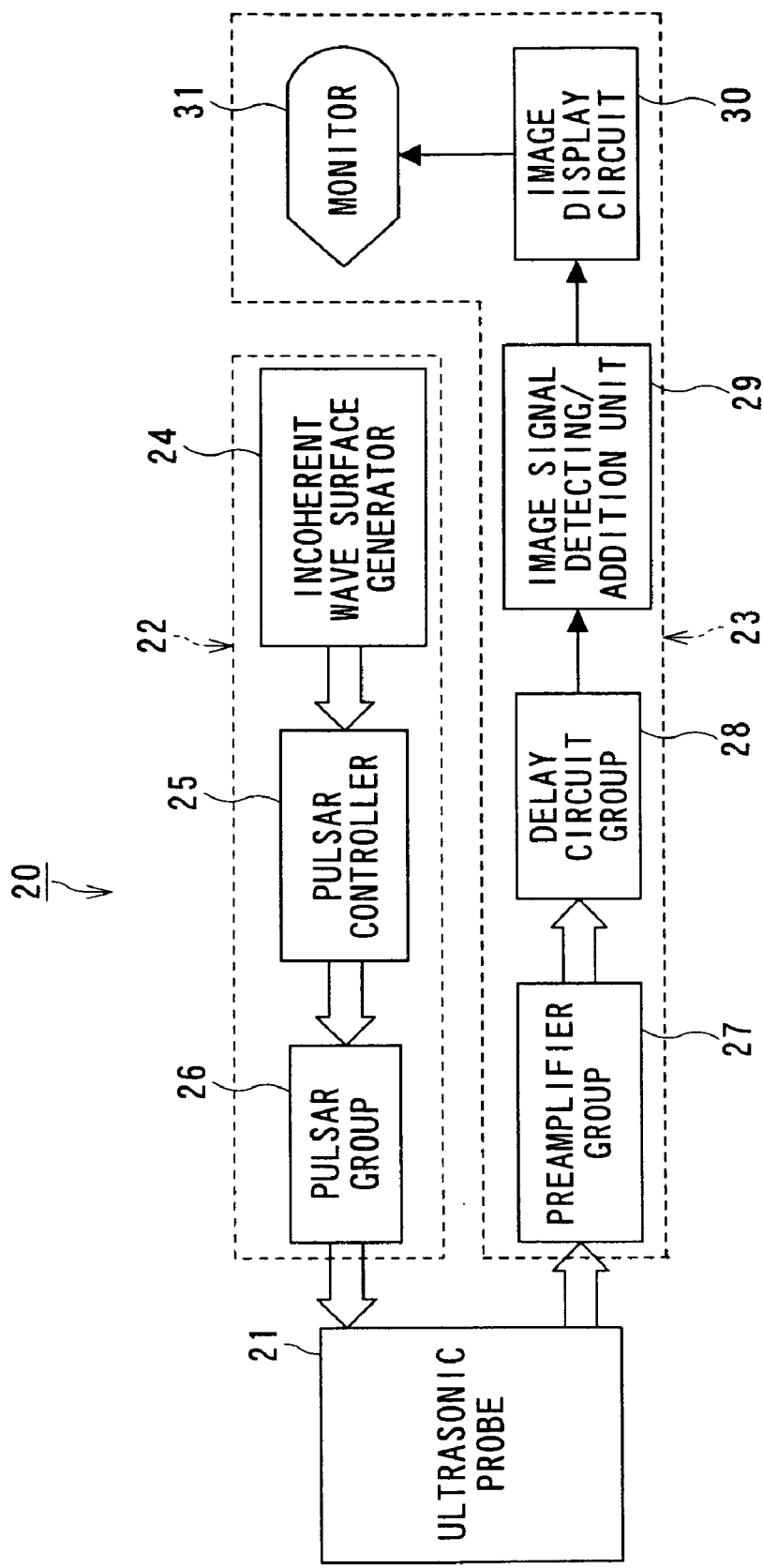
FIG. 1 is a block diagram showing an ultrasonic diagnostic apparatus according to an embodiment of the present invention.

FIG. 1 is a block diagram showing an ultrasonic diagnostic apparatus according to an embodiment of the present invention.

An ultrasonic diagnostic apparatus 20 includes an ultrasonic probe 21, an ultrasonic transmitting system 22 and an ultrasonic receiving system 23. The ultrasonic probe 21 is connected to the ultrasonic transmitting system 22 and the ultrasonic receiving system 23. The ultrasonic transmitting system 22 includes an incoherent wave surface generator 24, a pulsar controller 25 and a pulsar group 26. The ultrasonic receiving system 23 includes a preamplifier group 27, a delay circuit group 28, an image signal detecting/addition unit 29, an image display circuit 30 and a monitor 31.

The ultrasonic probe 21 has a ultrasonic minute oscillating element group, and includes the function of converting electric pulses received from the ultrasonic transmitting system 22 into ultrasonic wave signals in each of the minute oscillating elements respectively and transmitting the ultrasonic wave signals into the subject, and the function of receiving reflected waves generated in the subject and converting them into electric signals in each of the same minute oscillating elements respectively, then providing the electric signals to the ultrasonic receiving system 23, as reflected wave signals.

With the function of each structure member, the ultrasonic diagnostic apparatus 20 includes the following functions: a function as an ultrasonic transmitting unit for transmitting at least an ultrasonic wave that is neither a plane wave nor a wave having a focused wave surface, to the subject so that the wave surface of the ultrasonic wave temporally varies on the same scanning line; a function as image signal generating unit for generating an image signal from each of the reflected waves generated for each wave surface in the subject; and a function as a signal addition unit for mutually adding a plurality of signals obtained from reflected waves generated by a transmission ultrasonic wave or transmission ultrasonic waves with mutually different wave surface portions on the same scanning line, and thereby obtaining an image signal with speckle noise reduced.

As an ultrasonic waves to be transmitted to the subject, for example, an ultrasonic wave having a random wave surface with no focus provided, as a transmission wave surface, can be used. Specifically, if each ultrasonic wave that is a non-plane wave, such as an ultrasonic wave having a random wave surface, is transmitted so that the wave surface portions temporally vary on the same scanning line, mutually different phase interference patterns are obtained. Accordingly, a plurality of signals obtained from the reflected waves generated by a transmission ultrasonic wave or transmission ultrasonic waves with mutually different wave surface portions on the same scanning line are added to one another, and thereby an image signal with speckle noise reduced can be obtained.

Ordinary ultrasonic diagnostic apparatuses transmit an ultrasonic wave with a focused wave surface. However, because the ultrasonic wave with the focused wave surface exhibits behavior like a plane wave in the vicinity of a focus, the ultrasonic wave transmitted from the ultrasonic diagnostic apparatus 20 is required to be neither a plane wave nor a wave having a focused wave surface.

Therefore, the wave surface of an ultrasonic wave to be transmitted to the subject have only to be a wave surface such as to provide mutually different phase interference patterns, besides being a random wave surface. In other words, the wave surface of ultrasonic wave is not required to be perfectly random one, but has only to be a pseudo-random wave surface that can be regarded as being sufficiently random to the extent that allows mutually different phase interference patterns to be obtained.

Figure 2:
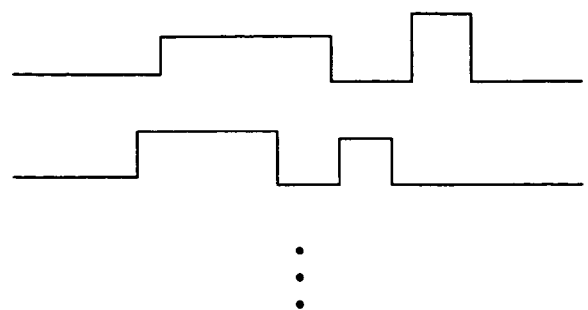
FIG. 2 is a diagram showing the first example of a wave surface of an ultrasonic wave which is to be transmitted to a subject from the ultrasonic probe of the ultrasonic diagnostic apparatus shown in FIG. 1.
Figure 3:
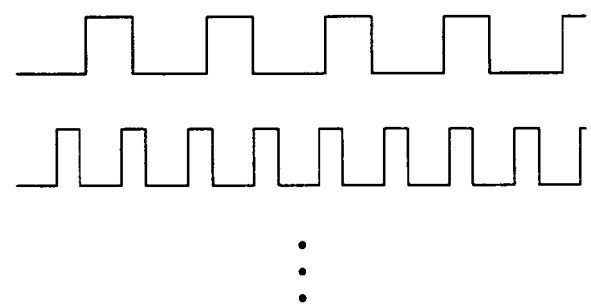
FIG. 3 is a diagram showing the second example of a wave surface of an ultrasonic wave which is to be transmitted to a subject from the ultrasonic probe of the ultrasonic diagnostic apparatus shown in FIG. 1.
Figure 4:
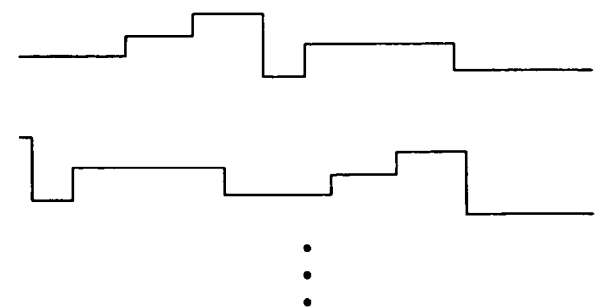
FIG. 4 is a diagram showing the third example of a wave surface of an ultrasonic wave which is to be transmitted to a subject from the ultrasonic probe of the ultrasonic diagnostic apparatus shown in FIG. 1.

FIG. 2 is a diagram showing the first example of a wave surface of an ultrasonic wave which is to be transmitted to a subject from the ultrasonic probe 21 of the ultrasonic diagnostic apparatus 20 shown in FIG. 1. FIG. 3 is a diagram showing the second example of a wave surface of an ultrasonic wave which is to be transmitted to a subject from the ultrasonic probe 21 of the ultrasonic diagnostic apparatus 20 shown in FIG. 1. FIG. 4 is a diagram showing the third example of a wave surface of an ultrasonic wave which is to be transmitted to a subject from the ultrasonic probe 21 of the ultrasonic diagnostic apparatus 20 shown in FIG. 1.

When a wave surface of an ultrasonic wave is made a pseudo-random wave surface, considering that it is undesirable that unwanted weights be put on image signals obtained for each wave surface portion, it is preferable that the amplitude distribution of the transmission wave surface of the ultrasonic wave be a substantially rectangular distribution or a distribution having a flat amplitude characteristic in a region to a certain extent.

Hence, the pseudo-random wave surface group that can be used may include a wave surface group in which the phases stepwise vary in a desirable limited region as shown in FIG. 2; a wave surface group having binary phases and being mutually different in period as shown in FIG. 3; and a wave surface group having N-value phases (N; integer) and being mutually different in the turn and/or period as shown in FIG. 4.

That is, even though a combination of a pseudo-random wave surface and a random wave surface or a pseudo-random wave surface is used as a wave surface of an ultrasonic wave, an effect similar to that in the case where a random wave surface is used as a wave surface of an ultrasonic wave, can be produced. Such being the case, descriptions hereinafter will be made on the premise that the random wave surface comprises a combination of a pseudo-random wave surface and a random wave surface or a pseudo-random wave surface.

Furthermore, a wave surface obtained by subjecting either of a random wave surface, a pseudo-random wave surface and a combined wave surface of a pseudo-random wave surface and a random wave surface to filtering with a desired characteristic allows the above-described effect to be obtain. Therefore, it is assumed that each of these filtered wave surfaces is one of random wave surfaces.

The methods for varying wave surface portions of an ultrasonic wave or ultrasonic waves on the same scanning line include: a method in which, while fixing the relative positional relationship between the subject and the ultrasonic wave transmitting/receiving surface of the ultrasonic probe 21, ultrasonic waves having a plurality of kinds of mutually different wave surfaces respectively are generated to thereby transmit them to the subject over a plurality of times; and a method in which an ultrasonic wave having a certain wave surface that is not a plane wave are transmitted continuously or intermittently while changing the relative positional relationship between the subject and the ultrasonic wave transmitting/receiving surface of the ultrasonic probe 21.

When using a random wave surface as a transmission wave surface of an ultrasonic wave, as approaches for generating a random transmission wave surface of an ultrasonic wave, a method using the reverse transmission of a random wave surface, and a method for approximately generating a random transmission wave surface of an ultrasonic wave by the Fourier transform, are known.

Figure 5:
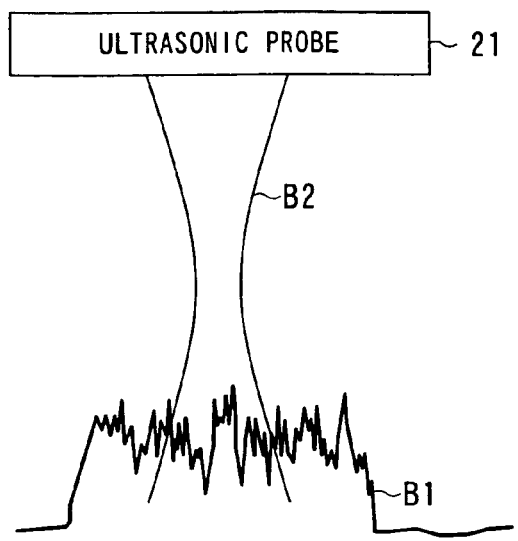
FIG. 5 is a diagram showing an example of an ultrasonic wave having a random wave surface which is to be transmitted to a subject from the ultrasonic probe of the ultrasonic diagnostic apparatus shown in FIG. 1.

FIG. 5 is a diagram showing an example of an ultrasonic wave having a random wave surface which is to be transmitted to a subject from the ultrasonic probe 21 of the ultrasonic diagnostic apparatus 20 shown in FIG. 1.

As shown in FIG. 5, when a transmission beam B1 with a random wave surface is formed by an ultrasonic wave transmitted from the ultrasonic probe 21 to the subject while providing a reception beam B2 with a focus, let a direction parallel to the transmitting/receiving surface of the ultrasonic probe 21 be x-direction, and let the depth direction of an ultrasonic wave perpendicular to the transmitting/receiving surface of the ultrasonic probe 21 be z-direction.

First, the method by the reverse transmission of a random wave surface will be explained using a coordinate system shown in FIG. 5.

In the case where a wave surface F(x, z, t) is needed at a desired distance x, z from the ultrasonic probe 21, at a time t, a signal to be detected in each of the ultrasonic minute oscillating elements of the ultrasonic probe 21 when subjecting a wave surface F(x, z, t) to the reverse transmission in the direction which faces to the ultrasonic probe 21, can be determined by the following expression (1):

$$f(\xi,0,t)=\int F(x,z,t-l(\xi,x,z)/c_0)G(l(\xi,x,z))dx \quad (1)$$

wherein $$l(\xi,x,z)=\sqrt{\overrightarrow{(\xi-x)^2+z^2}},$$

$$G(l)=1/\sqrt{l},$$

c0: the velocity of sound in a living body and
ξ: each position of the ultrasonic minute oscillating elements.

By the expression (1), an ultrasonic wave signal f(ξ, 0, t) to be transmitted to the subject from the ultrasonic minute oscillating element at a position ξ in the ultrasonic probe 21 can be obtained. Therefore, transmitting an ultrasonic wave signal f(ξ, 0, t) to the subject from each ultrasonic minute oscillating element at the position ξ, enables the formation of the random wave surface F(x,z,t).

However, transmitting the ultrasonic wave signal f(ξ, 0, t) itself from each of the ultrasonic minute oscillating elements results in transmitting ultrasonic waves having waveforms different from one ultrasonic minute oscillating element to another. This causes a problem in that the amount of data to be controlled in the ultrasonic transmitting system 22 increases. Accordingly, it is practical to convert the ultrasonic wave signal f(ξ, 0, t) into a delay time or a phase of a transmission signal, and transmit ultrasonic waves having the same waveform from the respective ultrasonic minute oscillating elements, with delay times or phases varied from one ultrasonic wave to another.

Next, a method of generating the random ultrasonic transmitted wave surface by the Fourier transform will be described.

In a remote field in which the Fresnel approximation holds, the transmission of ultrasonic waves can be approximated by the Fourier transform. Accordingly, approximating a transmission waveform of an ultrasonic wave by a continuous wave at a single frequency allows a transmission signal to be transmitted from each of the ultrasonic minute oscillating elements to the subject to be obtained. Specifically, in the coordinate system shown in FIG. 5, letting the center angular frequency of an ultrasonic wave be ω, and letting a desired random wave surface to be generated be a complex number F(x, z, ω), an ultrasonic wave signal f(ξ, 0, ω) to be transmitted to the subject from the ultrasonic minute oscillating element at the position ξ of the ultrasonic probe 21 can be obtained by the following expression (2).

$$f(\xi,0,\omega) = \int F(x,z,\omega)\exp\left\{-j\frac{\omega}{c_0}\frac{x\xi}{z^2}\right\}dx, \quad (2)$$

wherein ω represents a central angular frequency of an ultrasonic wave.

The ultrasonic wave signal f(ξ, 0, ω) obtained by the expression (2) is a complex signal to be transmitted to the subject from the ultrasonic minute oscillating element at the position ξ, and the phase and amplitude of the ultrasonic wave can be obtained from the complex signal f(ξ, 0, ω). Therefore, transmitting an ultrasonic wave pulse having the phase and amplitude obtained from the complex signal f(ξ, 0, ω), to the subject from each of the ultrasonic minute oscillating elements allows the random wave surface F(x, z, ω) to be formed. Also, converting the phase obtained from the complex signal f(ξ, 0, ω) into a delay time τ by the following expression (3) and transmitting ultrasonic wave pulses having the same phase and being temporally delayed, to the subject from the respective ultrasonic minute oscillating elements allows the random wave surfaces F(x, z, ω) to be formed, as well.

$$\tau=arg\{f(\xi,0,\omega)\}/\omega \quad (3)$$

In this way, transmission signals to be transmitted from the each of the ultrasonic minute oscillating elements to the subject can be obtained by the method using the reverse transmission of a random wave surface or the method with the Fourier transform. However, from the viewpoint of the sensitivity of the ultrasonic diagnostic apparatus 20, it is undesirable that the wave surface of the transmission ultrasonic wave spread more than necessary because it causes the reduction in energy efficiency. It is therefore effective from the view of the sensitivity of the ultrasonic diagnostic apparatus 20 that the random wave surface F serving as a basis when obtaining the transmission signal f to be transmitted to the subject from each of the ultrasonic minute oscillating elements are determined so that energy is concentrated on a required region.

One realistic example of a random wave surface F in which energy concentrates on a required region is a random wave surface in which the amplitude distribution is rectangular and in which the phase follows to uniform random numbers. In particular, when generating a random wave surface by the method using the Fourier transform, the multiplication between the amplitude distribution of the random wave surface F on the surface of an object irradiated with an rasonic wave, and the random number or determining the phase, is represented by a convolution of Fourier transforms of the amplitude distribution and the random number on the aperture surface of the ultrasonic probe 21. Hence, the random wave surface may also be determined by generating a random number in conformance with a complex normal distribution on the aperture surface of the ultrasonic probe 21, and taking convolution between the generated random number and a function obtained by Fourier transforming the amplitude distribution of a desired random wave surface on the surface of the object.

Furthermore, an ultrasonic wave itself having a random transmission wave surface obtained in this manner may be transmitted from the ultrasonic diagnostic apparatus 20, or alternatively, an ultrasonic wave having an approximate wave surface based on the above-described ultrasonic wave with the random wave surface, such as an approximate wave surface obtained by quantizing one or both of the phase and amplitude of the obtained random wave surface, may be transmitted from the ultrasonic diagnostic apparatus 20.

Transmitting the transmission signals obtained by one of the above-described approaches from each of the ultrasonic minute oscillating elements to the subject, allows the formation of a random wave surface. Specifically, the methods allowing the formation of a random wave surface include: a) a first method in which the waveform of a transmission signal transmitted from each of the ultrasonic minute oscillating elements is controlled to become a waveform f obtained by the method using the reverse transmission of a random wave surface or the method using the Fourier transform; b) a second method in which the waveform f obtained by the method using the reverse transmission of a random wave surface or the method using the Fourier transform is converted into one or both of the delay time $\tau$ and phase of a transmission signal transmitted from each of the ultrasonic minute oscillating elements and in which ones or both of the delay times $\tau$ and phases of the transmission signals is controlled; and c) a third method in which the first and second methods are combined.

Figure 6:
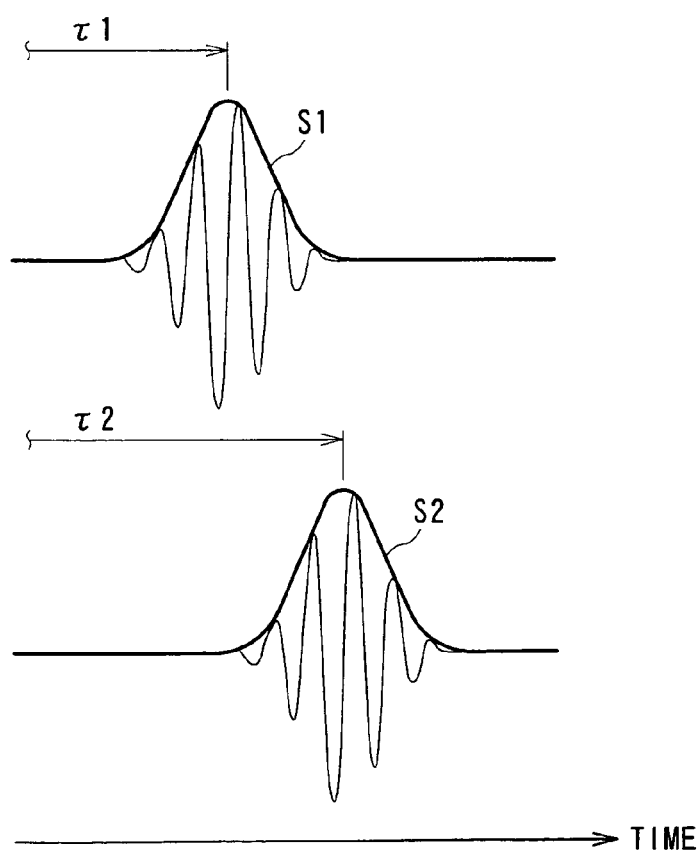
FIG. 6 is a diagram explaining an example of a controlling method of a delay time of a transmission signal of an ultrasonic wave which is to be transmitted to a subject from the ultrasonic probe of the ultrasonic diagnostic apparatus shown in FIG. 1.
Figure 7:
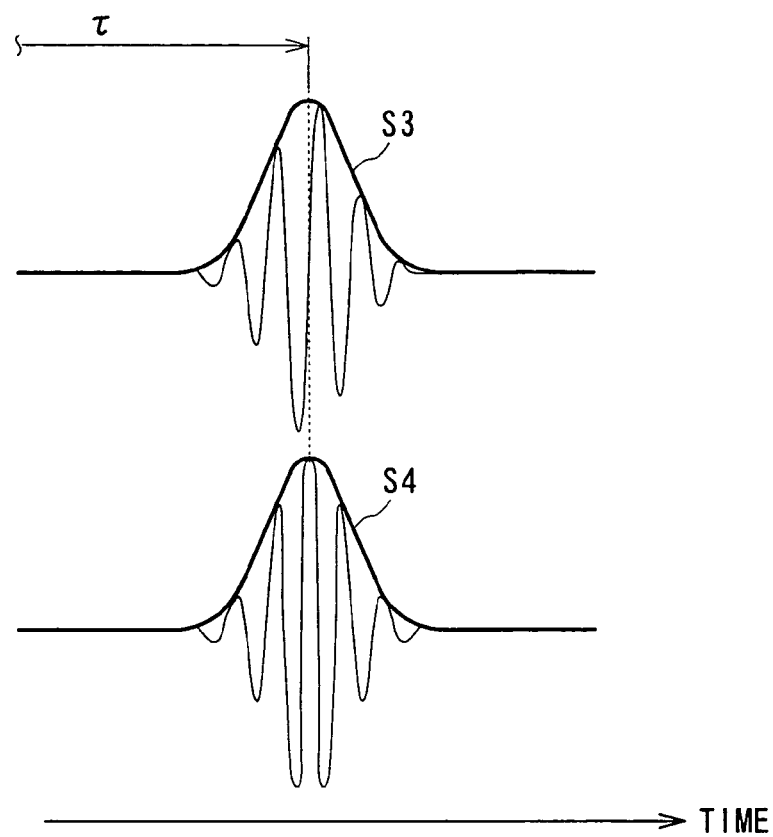
FIG. 7 is a diagram explaining an example of a controlling method of a phase of a transmission signal of an ultrasonic wave which is to be transmitted to a subject from the ultrasonic probe of the ultrasonic diagnostic apparatus shown in FIG. 1.

FIG. 6 is a diagram explaining an example of a controlling method of a delay time of a transmission signal of an ultrasonic wave which is to be transmitted to a subject from the ultrasonic probe 21 of the ultrasonic diagnostic apparatus 20 shown in FIG. 1. FIG. 7 is a diagram explaining an example of a controlling method of a phase of a transmission signal of an ultrasonic wave which is to be transmitted to a subject from the ultrasonic probe 21 of the ultrasonic diagnostic apparatus 20 shown in FIG. 1.

As shown in FIG. 6, for example, controlling delay times $\tau 1$ and $\tau 2$ of transmission signals transmitted from respective ultrasonic minute oscillating elements of the ultrasonic probe 21 allows a random wave surface to be formed. Specifically, from one ultrasonic minute oscillating element, a transmission signal S1 is transmitted with a delay of the delay time $\tau 1$ obtained by converting a waveform obtained by the method using the reverse transmission of a random wave surface or the method using the Fourier transform. From another ultrasonic minute oscillating element, a transmission signal S2 having the same waveform as that of the transmission signals S1 is transmitted with a delay of the delay time $\tau 2$ obtained by converting a waveform obtained by the method using the reverse transmission of a random wave surface or the method using the Fourier transform.

Also, as shown in FIG. 7, for example, controlling the phase of a transmission signal transmitted from each of the ultrasonic minute oscillating elements of the ultrasonic probe 21 allows the formation of a random wave surface. Specifically, from one ultrasonic minute oscillating element, a transmission signal S3 is transmitted with a delay of the delay time $\tau$. From another ultrasonic minute oscillating element, a transmission signal S4 that is phase-controlled so as to become a phase obtained by converting a waveform obtained by the method using the reverse transmission of a random wave surface or the method using the Fourier transform, is transmitted with a delay of the same delay time $\tau$ as that of the transmission signal S3. That is, this method for generating a random wave surface by the control of phase is a method in which the envelopes of waveforms of transmission signals are equalized for each of the ultrasonic minute oscillating elements, while varying the phase of a carrier wave.

Furthermore, another desirable method for generating a random wave surface is a method in which, with respect to the envelope of the transmission signals, delay control is performed to the energy center of a required transmission beam, and in which, regarding the carrier wave, a transmission signal such as to become a random phase is transmitted from each of the ultrasonic minute oscillating elements. According to such a generating method for a random wave surface, it is possible to realize, by a simple control, the formation of a wave surface superior in energy efficiency and having a sufficiently random phase. From the viewpoint of providing a wave surface with sufficiently fine randomness, it is recommended that the transmission aperture of the ultrasonic probe 21 be made large. Thereby, it is effective to transmit ultrasonic wave transmission signals from more ultrasonic minute oscillating elements, and preferably, from all of the ultrasonic minute oscillating elements of the ultrasonic probe 21.

The ultrasonic transmitting system 22 includes the function of generating required electric pulses and impressing them to ultrasonic minute oscillating element group in the ultrasonic probe 21, and thereby, as described above, controlling at least one of the waveform, delay time, and phase of each of the transmission signals transmitted from ultrasonic minute oscillating elements to the subject. Specifically, the ultrasonic transmitting system 22 includes at least one of the following functions: a function as a waveform control unit for controlling the waveform of a transmission signal transmitted from each of ultrasonic minute oscillating elements to the subject; a function as a timing control unit for controlling the generation timing of an electric pulse impressed to each of the ultrasonic minute oscillating elements; a function as a phase control unit for controlling the phase of the transmission ultrasonic wave transmitted from each of the ultrasonic minute oscillating elements; and a function as an amplitude control unit for controlling the amplitude of the transmission ultrasonic wave transmitted from each of the ultrasonic minute oscillating elements.

Specifically, the incoherent wave surface generator 24 has the function of generating control information with respect to transmission signals so that at least one of the waveform, delay time, and phase of a transmission signal transmitted from each of the ultrasonic minute oscillating elements to the subject, is controlled to allow a random wave surface to be formed, and providing the generated control information to the pulsar controller 25.

The pulsar controller 25 has the function, based on the control information with respect to the transmission signals received from the incoherent wave surface generator 24, of generating a control signal with respect to the pulsar group 26 such that the waveform, delay time, and phase of the transmission signal to be transmitted from each of the ultrasonic minute oscillating elements to the subject become a waveform, delay time, and phase in conformance with the control information; and giving the generated control information to the pulsar group 26 to thereby cause the pulsar group 26 to generate electric pulses in response to the control information on the transmission signal.

The pulsar group 26 includes the function of generating electric pulses based on the control signal received from the pulsar controller 25, and the function of impressing the generated electric pulses to the ultrasonic minute oscillating element group in the ultrasonic probe 21. As a result, from each of the ultrasonic minute oscillating elements in the ultrasonic probe 21, transmission signals with a waveform, delay time, and phase in conformance with the control information generated by the incoherent wave surface generator 24 are transmitted to the subject.

Meanwhile, the actual apparatus of the ultrasonic transmitting system 22 does not need to be physically configured so as to separate the incoherent wave surface generator 24, the pulsar controller 25, and the pulsar group 26 from one another, but has only to have an apparatus configuration virtually including their functions in response to a method for forming a random wave surface.

For example, when attempting to form a random wave surface by controlling the waveform of a transmission signal transmitted from each of the ultrasonic minute oscillating elements to the subject, to become a waveform obtained by the method using the reverse transmission of a random wave surface, the ultrasonic transmitting system 22 can be configured by interconnecting an analog signal generator and an high-voltage amplifier through a digital-to-analog (DA) converter.

In this case, an analog signal with a waveform $f(\xi, 0, t)$ is generated by the analog signal generator, then the generated analog signal is converted by the DA converter into a digital signal with the waveform $f(\xi, 0, t)$, and is given to the high-voltage amplifier. Furthermore, the digital signal with the waveform $f(\xi, 0, t)$ is amplified by the high-voltage amplifier, and as an electric pulse, it is impressed to each of the ultrasonic minute oscillating elements in the ultrasonic probe 21, thereby driving each of the ultrasonic minute oscillating elements. Then, from the ultrasonic minute oscillating elements in the ultrasonic probe 21, respective transmission signals with mutually different waveforms $f(\xi, 0, t)$ are transmitted to the subject, and a random wave surface $F(x, z, t)$ is formed.

In other words, the high-voltage amplifier functions as the pulsar group 26; the analog signal generator and DA converter function as the incoherent wave surface generator 24 and the pulsar controller 25, respectively; and the ultrasonic transmitting system 22 has a function as a waveform control unit for controlling the waveform of a transmission ultrasonic wave.

Also, for example, when attempting to form a random wave surface by controlling the delay time of a transmission signal transmitted from each of the the incoherent wave surface generator 24, the pulsar controller 25s to the subject, the arrangement may be such that, in the incoherent wave surface generator 24, the delay time is determined by converting the waveform obtained by the method using the reverse transmission of a random wave surface or the method using the Fourier transform, and that the determined delay time is given to the pulsar controller 25, as delay time information. Furthermore, when the pulsar controller 25 is arranged to function as a timing control unit for controlling the generation timing of an electric pulse by providing the pulsar group 26 with the control signal generated based on the delay time information, a transmission signal with a required delay time is transmitted from each of the ultrasonic minute oscillating elements, thereby allowing the formation of a random wave surface.

On the other hand, the ultrasonic receiving system 23 in the ultrasonic diagnostic apparatus 20 includes a function as an image signal generating unit for generating image signals from respective reflected waves generated for each wave surface portion in the subject, and a function as a signal addition unit for acquiring an image signal with speckle noise reduced by mutually adding a plurality of signals obtained from reflected waves generated by a transmission ultrasonic wave or transmission ultrasonic waves with mutually different wave surface portions on the same scanning line.

In the ultrasonic receiving system 23, the targets for addition processing for reducing speckle noise may include: besides image signals, the amplitudes and intensities of scanning line signals obtained by removing phase information from the image signals for the purpose of preventing the occurrence of a phase interference between signals to be mutually added, and the amplitudes and intensities of scanning line signals after compression.

The preamplifier group 27, the delay circuit group 28, the image signal detecting/addition unit 29, the image display circuit 30 and the monitor 31 in the ultrasonic receiving system 23 have their respective detailed functions so that the above-described functions is provided.

Specifically, the preamplifier group 27 has the function of receiving reflected wave signals from the ultrasonic minute oscillating element group of the ultrasonic probe 21, then amplifies them, and provides the amplified reflected signals to the delay circuit group 28.

The delay circuit group 28 has a function as a reception beam former for forming a reception beam of reflected waves by performing delay addition of reflected wave signals received from the preamplifier group 27, and the function of generating a scanning line RF signal of the reflected waves by forming the aforementioned reception beam.

The image signal detecting/addition unit 29 includes the function of receiving the scanning line RF signals from the delay circuit group 28 and acquiring image signals by detecting/compressing the received scanning line RF signals; and the function of acquiring an image signal with speckle noise reduced by adding the image signals to one another. Here, the addition of the image signals may be a weighted addition as required.

The image display circuit 30 includes the function of receiving the image signal after addition, have been reduced in speckle noise, from the image signal detecting/addition unit 29, and converting the image signal into a luminance signal of an image mapped in accordance with the signal intensities; and the function of providing the obtained luminance signal to the monitor 31.

Next, the operation of the ultrasonic diagnostic apparatus 20 will be described.

A random wave surface is determined in advance, and then the waveform, delay time, and phase of a transmission signal from each of the ultrasonic minute oscillating elements, necessary for forming the random wave surface inside the subject, are determined. The waveform, delay time, and phase of the transmission signal are given from the incoherent wave surface generator 24 to the pulsar controller 25, as control information. Based on the control information received from the incoherent wave surface generator 24, the pulsar controller 25 generates a control signal with respect to the pulsar group 26 such that the waveform, delay time, and phase of the transmission signal transmitted from each of the ultrasonic minute oscillating elements to the subject become a waveform, delay time, and phase in conformance with the control information, and gives the generated control signal to the pulsar group 26. Then, based on the control signal received from the pulsar controller 25, the pulsar group 26 generates electric pulses of waveforms, delay times, and phases in response to the control information, and impressed them to the ultrasonic minute oscillating element group in the ultrasonic probe 21.

As a result, a transmission signal of a waveform, delay time, and phase in conformance with the control information generated in the incoherent wave surface generator 24 is transmitted from each of the ultrasonic minute oscillating elements in the ultrasonic probe 21 to the subject, thereby forming a desired random wave surface that have been determined in advance.

Furthermore, reflected waves generated by the transmission ultrasonic wave having the random wave surface inside the subject are received by the same ultrasonic minute oscillating element group in the ultrasonic probe 21, and are provided to the preamplifier group 27. In the preamplifier group 27, the reflected signals received from the ultrasonic minute oscillating element group are amplified, and the amplified reflected waves are provided to the delay circuit group 28. In the delay circuit group 28, a delay addition of the reflected wave signals received from the preamplifier group 27 is performed, and a reception beam of the reflected waves on desired scanning line is formed. Thereby, scanning line RF signals of the reflected waves are generated in the delay circuit group 28.

Next, the scanning line RF signals generated in the delay circuit group 28 are given to the image signal detecting/addition unit 29, in which the scanning line RF signals are detected/compressed to thereby obtain image signals. Here, because scattering waves generated by a large number of scattering objects existing within the subject cause a phase interference with one another, each the image signals involves a speckle noise of a pattern in response to the random wave surface of the transmission signal.

Then, in the same procedure, by the control of waveform, delay time, and phase on the transmission signal, an ultrasonic wave having a different random wave surface is transmitted on the same scanning line inside the subject, and image signals with speckle noises of speckle patterns in response to the newly formed random wave surface are generated in the image signal detecting/addition unit 29.

Moreover, such an ultrasonic wave having a different random wave surface is repetitively transmitted over a plurality of times by a desired number of times, and thereby image signals each having a speckle pattern mutually different by the number of random wave surfaces are obtained in the image signal detecting/addition unit 29. Then, the plurality of obtained image signals each having a mutually different speckle pattern are added to one another in the image signal detecting/addition unit 29, and thereby an image signal with speckle noise reduced can be obtained. Therefore, obtaining more image signals each having a mutually different speckle pattern on the same scanning line, allows the enhancement of a speckle reducing effect. This being the case, the number of transmissions of ultrasonic waves is determined in accordance with the degree of a required speckle reducing effect.

Here, the methods for transmitting ultrasonic waves having mutually different random wave surfaces on the same scanning line over a plurality of times may include: a method for transmitting ultrasonic waves having mutually different random wave surfaces from the respective ultrasonic minute oscillating elements over a plurality of times as described above; and a method in which an ultrasonic wave having a random wave surface is once transmitted from the respective ultrasonic minute oscillating elements, and in which the relative positional relationship between the subject and each of the ultrasonic minute oscillating elements is shifted so that ultrasonic waves having mutually different random wave surfaces are transmitted substantially on the same scanning line over a plurality of times.

When attempting to generate a plurality of image signals on the same scanning line in a time series, a speckle reducing effect can also be obtained by the "persistence" method, which is a technique conventionally used for ultrasonic diagnostic apparatuses. Specifically, when an image signal of a certain frame has been generated, an image signal in a single frame in the past or the weighted sum of image signals corresponding to a plurality of frames in the past, and the newly generated image signal are added with weighting, whereby an effect of improving real time characteristic and smoothing images is produced, as well as an image signal with a speckle reducing effect improved can be obtained.

While electronic scanning is performed over a scanning line in a scanning direction, and thereby all image signals in a required range are collected, a scanning method will now be described.

Between mutually different scanning lines, transmission signals having the same random wave surface group may be transmitted, or alternatively, wave surface groups may be arranged to be mutually different from one scanning line to another. However, from the viewpoint of improving the uniformity of image signals ultimately obtained, it is desirable to transmit transmission signals with the same random wave surface group between mutually different scanning lines.

Even when attempting to generate a plurality of image signals on the same scanning line in a time series, transmission signals with a group of random wave surfaces that are equal for each frame may be transmitted, or alternatively, wave surfaces may be arranged to be different from one frame to another. However, since a speckle reducing effect can also be obtained by the "persistence" method, which is a technique conventionally used for ultrasonic diagnostic apparatuses, it is desirable to transmit ultrasonic waves with random wave surfaces mutually different from one frame to another.

In the above-described scanning method, the number of transmitting/receiving operations with respect to ultrasonic waves necessary to obtain a single image is given by the product of the number of scanning lines and the number of the image signals to be added. As a result, concerns arises that the real time characteristic in the above-described case may become inferior to that in the case of the conventional ultrasonic diagnostic apparatus, in which no reducing treating of speckle noise is performed. With this being the situation, a concurrent use of the parallel signal processing technique capable of obtaining reception signals on a plurality of scanning lines by a single transmitting operation, allows the avoidance of the deterioration of real time characteristic.

Figure 8:
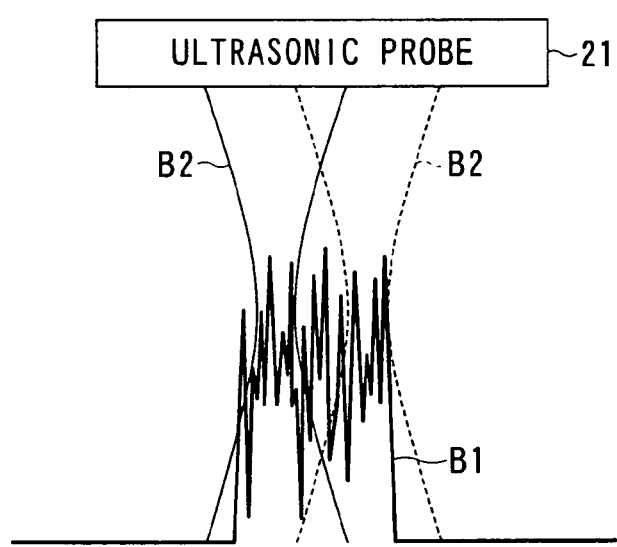
FIG. 8 is a diagram explaining a method of scanning so that a transmission signal of an ultrasonic wave having a random wave surface is transmitted from the ultrasonic probe of the ultrasonic diagnostic apparatus shown in FIG. 1 to receive reflected wave signals with the parallel signal processing.

FIG. 8 is a diagram explaining a method of scanning so that a transmission signal of an ultrasonic wave having a random wave surface is transmitted from the ultrasonic probe 21 of the ultrasonic diagnostic apparatus 20 shown in FIG. 1 to receive reflected wave signals with the parallel signal processing.

As shown in FIG. 8, the parallel signal processing technique is a technique by which an ultrasonic wave is transmitted/received with respect to the ultrasonic probe 21 to thereby form a transmission beam B1 having a random wave surface with a fixed width, while arranging a plurality of reception beams B2 within the width of the wave surface of the transmission beam B1 to thereby simultaneously obtain signals on a plurality of scanning lines. In FIG. 8, an example is shown in which two reception beams B2 indicated by a dotted line and solid line are arranged. Transmitting an ultrasonic wave with a random wave surface on scanning lines by desired times so that its wave surface varies for each scanning line, allows a plurality of image signals, in accordance with a number of transmission operations, each having a speckle noise pattern mutually different from one scanning line to another, to be obtained. Furthermore, mutually adding image signals for each scanning line enables image signals with speckle noise reduced in accordance with a number of transmission operations, to be obtained on a plurality of scanning lines.

Next, by moving the positions of transmission wave surfaces in the scanning direction and performing the transmission of ultrasonic waves and the addition of image signals as above-described, i.e., by performing a transmission wave surface scanning, image signals over the entire range can be obtained.

According to this scanning method concurrently using the parallel signal processing technique, the number of transmitting/receiving operations with respect to ultrasonic waves necessary to obtain a single image becomes a number obtained by dividing the product of the number of scanning lines and the number of image signals to be added by the number of the reception beams B2 arranged for the parallel signal processing, so that an improvement in real time characteristic can be achieved. For example, when the number of image signals to be added is four, if the number of the reception beams B2 arranged for the parallel signal processing is four, it is possible to obtain the same real time characteristic as the imaging of the conventional ultrasonic diagnostic image involving no addition for obtaining speckle noise reducing effect.

However, in the scanning method concurrently using the parallel signal processing technique, the timing for changing the wave surface position of a transmission signal becomes a point in time when the transmission/reception time interval of ultrasonic waves has elapsed by a time corresponding to the number of image signals to be added, so that a problem arises that a stepwise time phase difference occurs between scanning lines. For example, when the number of image signals to be added is four and the number of the reception beams B2 for the parallel signal processing is four, among the image signals obtained from the four reception beams B2 for the parallel signal processing, there is no time phase difference. However, between each of the image signals obtained from the above-described four scanning lines for the parallel signal processing, and a respective one of the image signals obtained from subsequent four scanning lines that are adjacent to the above-described four scanning lines along the scanning direction, there occurs a time phase difference corresponding to the time interval of four times of ultrasonic wave transmission/reception operations.

This being the case, when the relative speed between an object to be imaged and the ultrasonic probe 21 is relatively high as in the case where the ultrasonic probe 21 is quickly moved or in attempting to obtain an image of a moving object, a step difference can occur in an obtained image.

Accordingly, when performing the parallel signal processing, performing the movement of the ultrasonic probe 21 and the transmission/reception of ultrasonic waves so that the time phase difference between scanning lines becomes more uniform, allows the above-described problem to be avoided.

Figure 9:
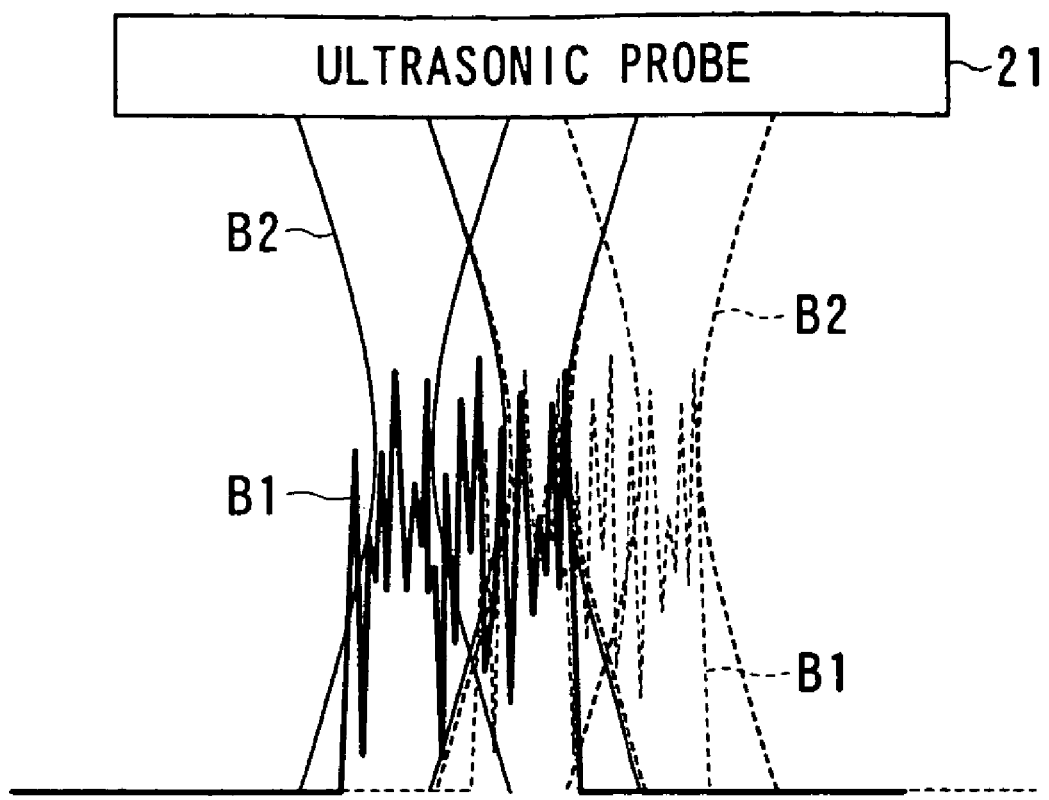
FIG. 9 is a diagram explaining an example of a transmission and reception method of an ultrasonic wave and a moving method of the ultrasonic probe for performing the parallel signal processing represented in FIG. 8.
Figure 10:
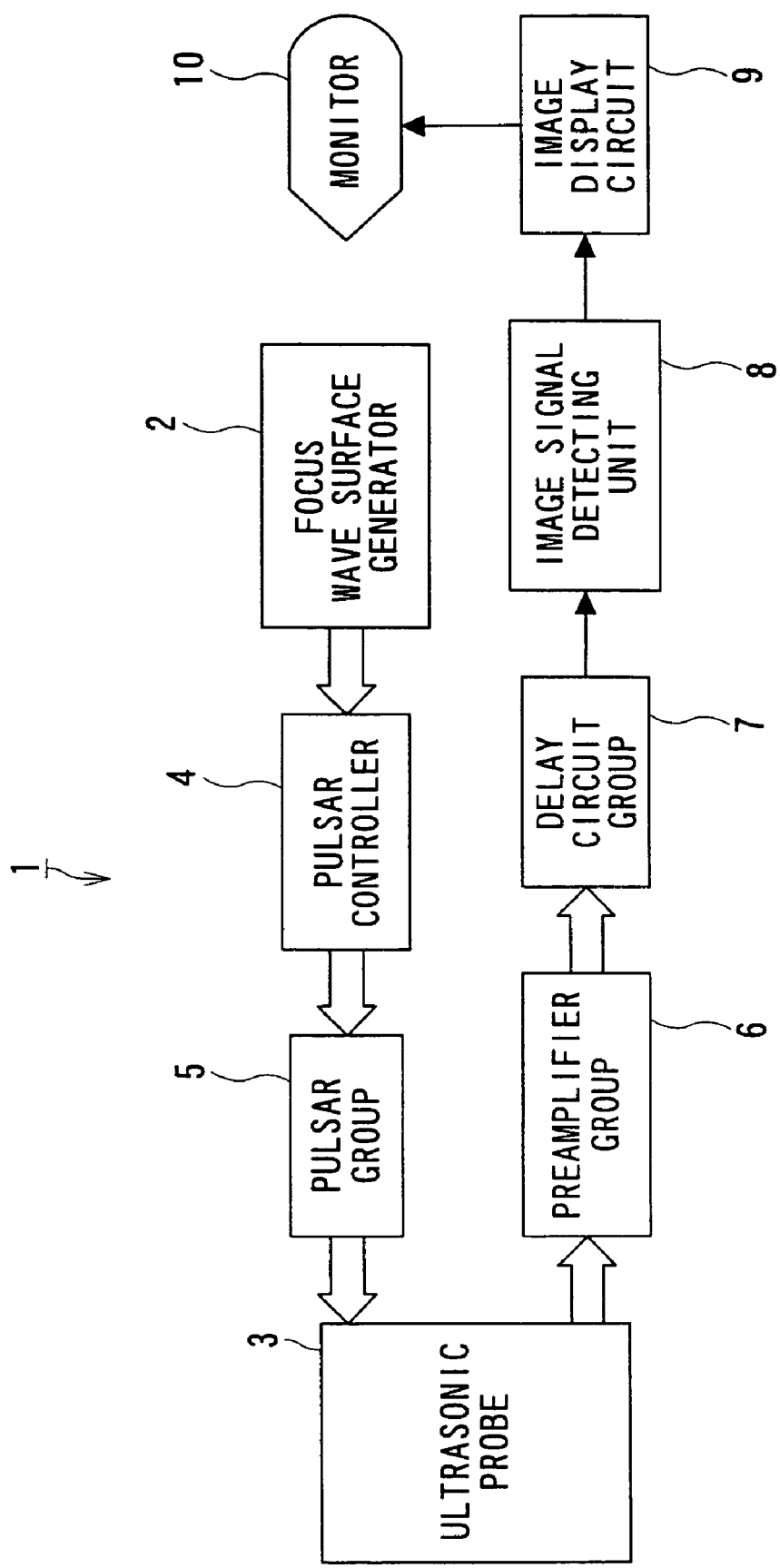
FIG. 10 is a block diagram of a conventional ultrasonic diagnostic apparatus.
Figure 11:
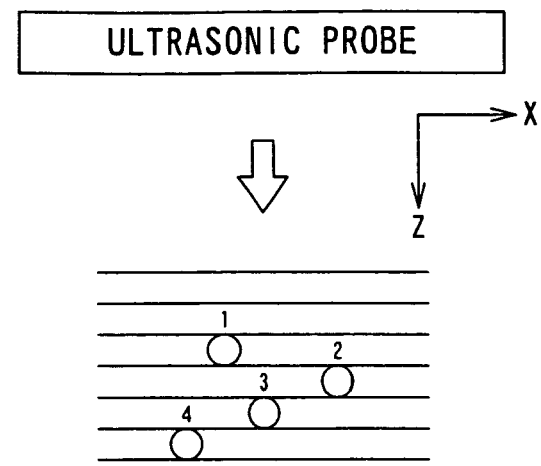
FIG. 11 is a diagram showing an example of wave surface of ultrasonic wave which is to be transmitted to a subject in a perpendicular direction in the case that an image is generated with the conventional spatial compound technology.
Figure 12:
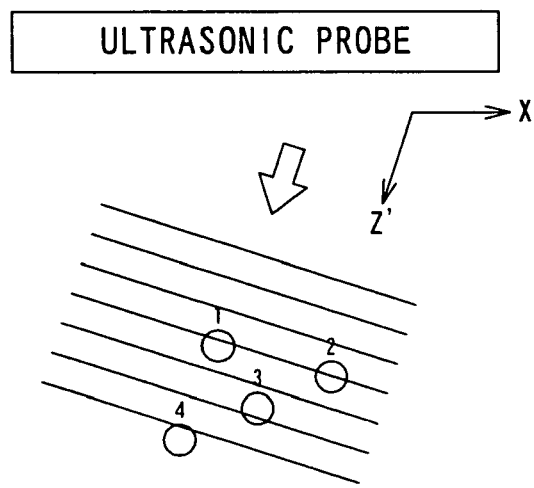
FIG. 12 is a diagram showing an example of wave surface of ultrasonic wave which is to be transmitted to a subject in the direction of oblique in the case that an image is generated with the conventional spatial compound technology.
Figure 13:
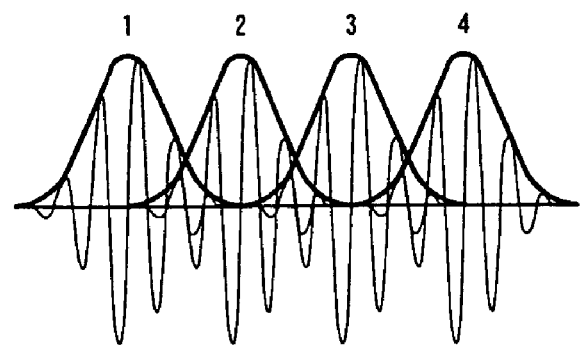
FIG. 13 is a diagram showing waveform of the scattering wave produced with the scattering object when the ultrasonic wave is transmitted so that the wave surface of the plane wave becomes vertical to the direction X of the transmission-and-reception face of the ultrasonic probe as shown in FIG. 11.
Figure 14:
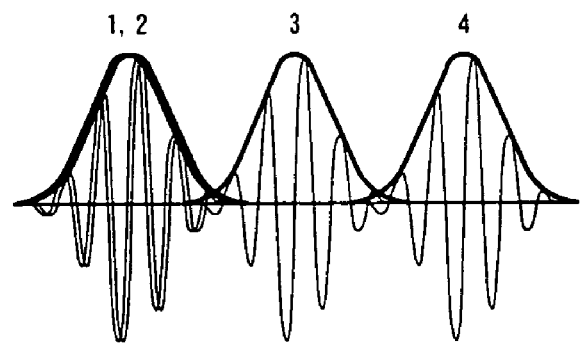
FIG. 14 is a diagram showing waveform of the scattering wave produced with the scattering object when the ultrasonic wave is transmitted so that the wave surface of the plane wave inclines to the direction X of the transmission-and-reception face of the ultrasonic probe as shown in FIG. 12.
Figure 15:
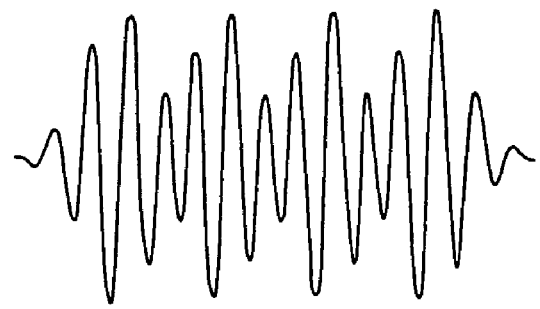
FIG. 15 is a diagram showing the result of interference on the scattering waves shown in FIG. 13.
Figure 16:
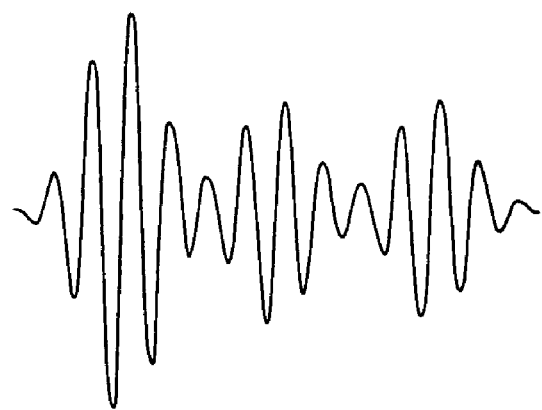
FIG. 16 is a diagram showing the result of interference on the scattering waves shown in FIG. 14.
Figure 17:
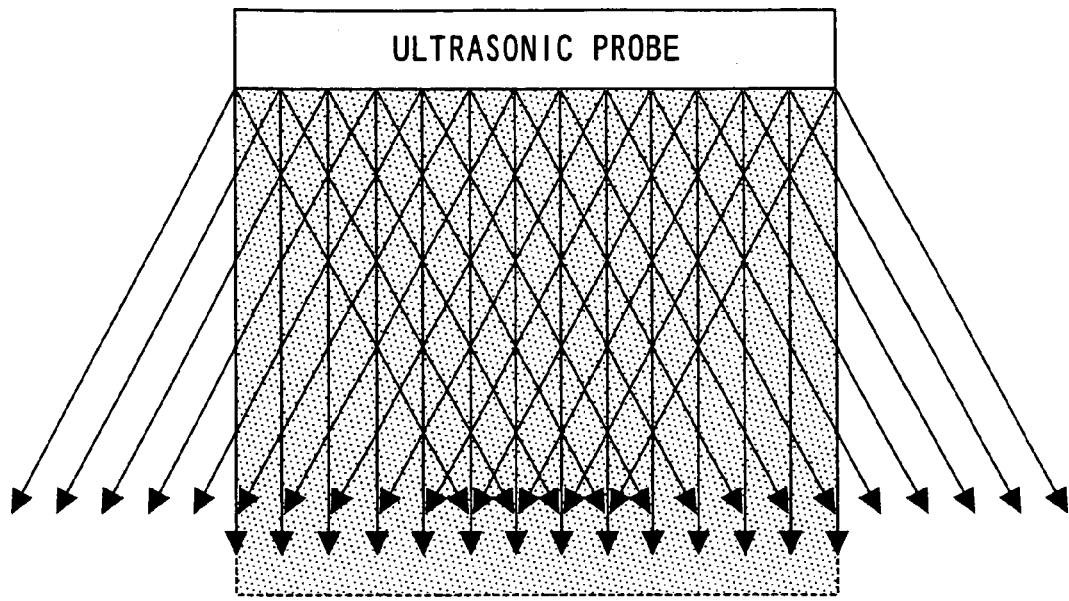
FIG. 17 is a diagram showing an example of scanning direction by the ultrasonic wave in case that an image is generated with the conventional spatial compound technology.
Figure 18:
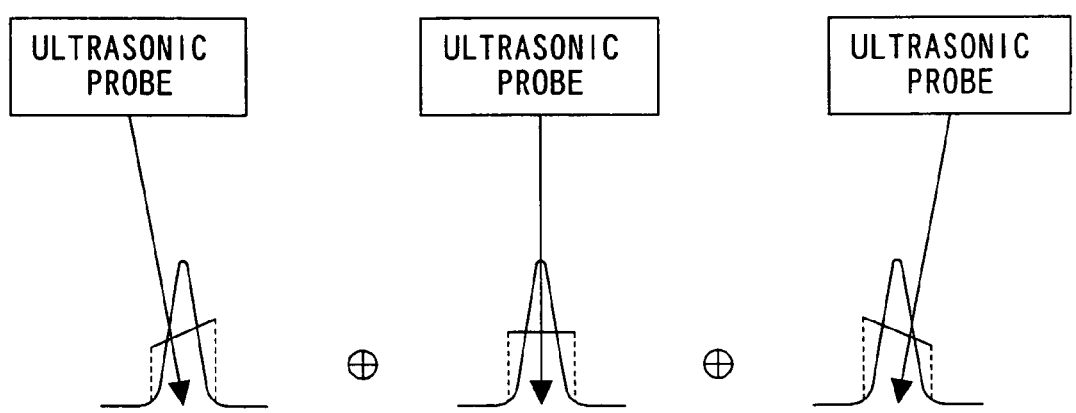
FIG. 18 is a conceptual diagram explaining the way of generating images with spatial compounding using data obtained by scanning in the scanning direction shown in FIG. 17.

FIG. 9 is a diagram explaining an example of a transmission and reception method of an ultrasonic wave and a moving method of the ultrasonic probe 21 for performing the parallel signal processing represented in FIG. 8.

First, as indicated by a solid line in FIG. 9, an ultrasonic wave transmission signal is transmitted so as to form a transmission beam B1 having a random wave surface with a finite width, and a plurality of reception beams B2 are arranged so as to be on the wave surface of the ultrasonic wave transmission signal, whereby image signals are obtained from a plurality of scanning lines by the parallel signal processing. Next, as indicated by a dotted line in FIG. 9, the wave surface of a transmission beam B1 is moved by a width corresponding to scanning lines of an arbitrary number, and the position of each of the reception beams B2 for the parallel signal processing is also moved by the width corresponding to scanning lines of the same number. In other words, scanning is performed so that the wave surface of the transmission beams B1 and the position of each of the reception beams B2 are mutually superimposed in the range corresponding to scanning lines of the arbitrary number.

Likewise, obtaining image signals while moving the wave surface of the transmission beam B1 and the position of each of the reception beams B2 for the parallel signal processing by the width corresponding to scanning lines of the same number; and then adding the obtained image signals from one scanning line to another, allows image signals temporally more uniform and having been reduced in speckle noise, to be obtained.

For example, when the number of reception beams for the parallel signal processing is four, by moving the wave surface of the transmission beam B1 by width corresponding to one scanning line as well as moving the position of each of the reception beams B2 by width corresponding to one scanning line, it is possible to obtain image signals each having a mutually different speckle pattern regarding the three superimposed scanning lines. At this time, because the image signals to be obtained from the three superimposed scanning lines are obtained from reflected waves at mutually different positions of the random wave surface, they become image signals each involving a mutually different speckle pattern. Similarly, by adding the obtained image signals to one another while moving the wave surface of the transmission beams B1 and the position of each of the reception beams B2 by width corresponding to one scanning line, one image signal with speckle noise reduced for each of the scanning lines can be obtained.

In addition, FIG. 9 is given assuming that the number of receiving beams on the parallel signal processing is two to simplify explanation. The wave surface of the transmission beam B1 and reception beam B2 after moving by one scanning line are indicated with dotted lines respectively. The wave surface of the transmission beam B1 and reception beam B2 before moving are indicated with solid lines respectively.

Generating image signals by such movement of the ultrasonic probe 21 and the transmission/reception method for an ultrasonic wave enables image signals temporally more uniform to be obtained. In particular, when moving the wave surface of the transmission beam B1 and the position of each of the reception beams B2 by width corresponding to one scanning line, the time phase difference between adjacent scanning lines become a time period of one transmission/reception operation as well as image signals are added by the number of operations with parallel signal processing so that image signals that are even more uniform temporally can be obtained. Furthermore, as a secondary effect, since random wave surfaces of ultrasonic wave transmission signals for obtaining image signals become the same among the scanning lines, spatially more uniform image signals can also be obtained.

The method for acquiring speckle noise reducing effect is not limited to the above-described method. A speckle noise reducing effect by the persistence method in which an image signal obtained with an addition and a subsequent image signal obtained with a transmission of an ultrasonic wave having a different random wave surface are added with weighting, can also be achieved. When attempting to obtain the speckle noise reducing effect by the persistence method, ten is sufficiently large for the number of kinds of random wave surfaces of ultrasonic transmission signals to be changed. Even under the persistence method, when the number of reception beams for the parallel signal processing is four, because image signals having forty kinds of speckle patterns can be obtained, a sufficient speckle noise reducing effect can be expected.

In the conventional spatial compound technique, the number of speckle patterns is not more than ten as well as the independence of an image signal having each individual speckle pattern is low. However, according to the technique using an ultrasonic wave with a random wave surface of the present ultrasonic diagnostic apparatus 20, a significant speckle noise reducing effect can be expected, as compared with the spatial compound technique.

The image signal after addition, having been reduced in speckle noise by the above-described methods, is given from the image signal detecting/addition unit 29 to the image display circuit 30. Then, the image display circuit 30 converts the image signal received from the image signal detecting/addition unit 29 into a luminance signal of an image mapped in accordance with the signal intensities, and gives the luminance signal to the monitor 31. As a consequence, on the monitor 31, an image inside the subject is displayed by luminance, the image having been reduced in speckle noise.

That is, the above-described ultrasonic diagnostic apparatus 20 does not vary ultrasonic wave transmission/reception angle for taking an image unlike the conventional spatial compound technique, but transmits an ultrasonic wave transmission signal having a wave surface of random phase, to the subject, while varying a wave surface by a plurality of times, and thereby the present ultrasonic diagnostic apparatus 20 obtains image signals each having a mutually different speckle pattern as well as reduces speckle noise by adding the plurality of the obtained image signals.

Therefore, according to the ultrasonic diagnostic apparatus 20, it is possible to obtain an image with speckle noise properly reduced by maintaining the number of scanning lines of image obtainable by the conventional ultrasonic diagnostic apparatus, and simultaneously, only by performing a relatively easy processing similar to that performed in the conventional ultrasonic diagnostic apparatus. Thus, since the ultrasonic diagnostic apparatus 20 can obtain a large number of mutually different speckle patterns that are independent of one another, by the number of random wave surfaces of transmission signals to be generated, a significant speckle reducing effect can be expected.

In the speckle noise reducing method by the conventional spatial compound, an image is obtained by transmitting/receiving ultrasonic waves with respect to mutually different directions, so that a transmission aperture is inevitably limited, and the sizes of inherently occurring speckles become large. In contrast, according to the ultrasonic diagnostic apparatus 20, the full aperture of the ultrasonic probe 21 can always be used as a transmission aperture, thereby allowing the sizes of speckles to become small, and even closer images to be obtained.

Moreover, it is possible to avoid the deterioration of real time characteristic by, while using a wide transmission beam having a random wave surface (phase) as a transmission beam, concurrently using the parallel signal processing technique, in which reception beams are arranged so as to be able to simultaneously receive reflected wave signals on a plurality of scanning lines in a transmission beam. At this time, obtaining image signals while moving the wave surface of an ultrasonic wave transmission signal and the position of each of the reception beams by width corresponding to one scanning line, enables the reduction in the image step difference due to a movement of an object and that due to the parallel signal processing. That is, by performing scanning using the transmission beam having the same wave surface while varying the position of the transmission beam with respect to a certain scanning line, it is possible to obtain image signals each having an independent speckle pattern on the respective scanning lines, and then add them. This allows the reduction in speckle noise without reducing the number of frames.

Regarding the scanning taking advantage of random wave surface according to the ultrasonic diagnostic apparatus 20, the scanning method by the ultrasonic probe 21 is not limited. Possible scanning methods by the ultrasonic probe 21 include sector scanning, linear scanning, convex scanning, and trapezoid scanning. In recent years, even in the harmonic imaging method, in which an image is obtained using harmonic components generated in a living body or a contrast medium, the technique according to present invention taking advantage of a random wave surface, makes it possible to obtain speckle patterns mutually different in the same manner as described above and to expect a speckle noise reducing effect.

What is claimed is:

1. An ultrasonic diagnostic apparatus comprising:
   an ultrasonic transmitting unit configured to transmit a plurality of ultrasonic waves each having a wave surface except a plane wave surface and a focused focal wave surface toward a plurality of scanning lines to construct an image of a subject so that shapes of wave surfaces of the ultrasonic waves temporally change on a same scanning line;
   an image signal generating unit configured to receive reflected waves produced by the wave surfaces and to generate first image signals according to the received reflected waves; and
   a signal addition unit configured to obtain a second image signal by adding the first image signals generated by the reflected waves produced by different wave surfaces of the transmitted ultrasonic waves on the same scanning line.

2. The ultrasonic diagnostic apparatus according to claim 1, wherein the ultrasonic transmitting unit is configured to generate the ultrasonic waves by controlling at least one of a phase and an amplitude of the ultrasonic waves.

3. An ultrasonic diagnostic apparatus according to claim 1, wherein the ultrasonic transmitting unit comprises:
   an ultrasonic probe including an ultrasonic minute oscillating element group; and
   a pulsar group configured to apply electric pulses to the ultrasonic minute oscillating element group so that the ultrasonic minute oscillating element group transmits the ultrasonic waves to the subject,
   the ultrasonic diagnostic apparatus further comprising at least one of a timing control unit configured to control a timing of generating the electric pulses; a waveform control configured to control a waveform of the ultrasonic wave to be transmitted from the ultrasonic minute oscillating element group; a phase control unit configured to control a phase of the ultrasonic waves to be transmitted from the ultrasonic minute oscillating element group; and an amplitude control unit configured to control an amplitude of the ultrasonic waves to be transmitted from the ultrasonic minute oscillating element group.

4. The ultrasonic diagnostic apparatus according to claim 1, wherein the ultrasonic transmitting unit is configured to generate ultrasonic waves having mutually different kinds of wave surfaces except the plane wave surface and the focused focal wave surface.

5. The ultrasonic diagnostic apparatus according to claim 1, wherein the image signal generating unit is configured to generate the first image signals according to the reflected waves by arranging receive beams so that the reflected waves produced on each scanning line of the scanning lines can be received.

6. The ultrasonic diagnostic apparatus according to claim 1, wherein the image signal generating unit is configured to receive the first reflected waves produced by the wave surfaces on the same scanning line substantially with a scan making positions of receive beams move so that at least one of the positions of the receive beams overlaps, the receive beams being arranged so as to receive each reflected wave from different scanning lines respectively.

7. The ultrasonic diagnostic apparatus according to claim 1, wherein the signal addition unit is configured to obtain the second image signal of which speckle noise is reduced by performing a weighted addition to a new image signal ,generated by the image signal generating unit, of a newly generated frame and a result value of another weighted addition to past image signals corresponding to at least two different past frames ,and
wherein the past image signals include at least one of the first image signals and the second image signal.

8. The ultrasonic diagnostic apparatus according to claim 1, wherein the ultrasonic transmitting unit is configured to transmit the ultrasonic waves having a random wave surface to the subject.

9. The ultrasonic diagnostic apparatus according to claim 1, wherein the ultrasonic transmitting unit is configured to transmit the ultrasonic waves to the subject so that phases of the wave surface portions change mutually in time and each shape of the wave surfaces temporally changes.

10. An ultrasonic diagnostic apparatus comprising:
an ultrasonic transmitting unit configured to transmit a plurality of ultrasonic waves of which a phase value varies according to a wave surface toward a plurality of scanning lines to construct an image of a subject so that shapes of wave surfaces of the ultrasonic waves temporally change on a same scanning line;
an image signal generating unit configured to the receive reflected waves produced by the wave surfaces and to generate first image signals according to the received reflected waves; and
a signal addition unit configured to obtain a second image signal by adding the first image signals generated by the reflected waves produced by different wave surfaces of the transmitted ultrasonic waves on the same scanning line.

11. An ultrasonic diagnostic method, implemented on an ultrasonic diagnostic apparatus, comprising:
transmitting a plurality of ultrasonic waves having a wave surface except a plane wave surface and a focused focal wave surface toward a plurality of scanning lines to construction an image of a subject so that shapes of wave surfaces of the ultrasonic waves temporally change on a same scanning line;
receiving reflected waves produced by the wave surfaces and generating first image signals according to the received reflected waves; and
obtaining a second image signal by adding the first image signals generated by the reflected waves produced by different wave surfaces of the transmitted ultrasonic waves on the same scanning line.

12. The ultrasonic diagnostic method according to claim 11, wherein the ultrasonic waves are generated by controlling at least one of a phase and an amplitude of the ultrasonic wave.

13. The ultrasonic diagnostic method according to claim 11, further comprising:
controlling a timing of generating the electric pulses to be applied to an ultrasonic minute oscillating element group included in an ultrasonic probe so that the ultrasonic waves are transmitted to the subject;
controlling a waveform of the ultrasonic waves to be transmitted from the ultrasonic minute oscillating element group;
controlling a phase of the ultrasonic waves to be transmitted from the ultrasonic minute oscillating element group; and
controlling an amplitude of the ultrasonic waves to be transmitted from the ultrasonic minute oscillating element group.

14. The ultrasonic diagnostic method according to claim 11, wherein the transmitting step transmits ultrasonic waves having mutually different kinds of wave surfaces except the plane wave surface and the focused focal wave surface.

15. The ultrasonic diagnostic method according to claim 11, wherein the generating step generates the first image signals according to the reflected waves by arranging receive beams so that the reflected waves produced on each scanning line of the scanning lines can be received.

16. The ultrasonic diagnostic method according to claim 11, wherein the receiving step receives the reflected waves produced by the wave surfaces on the same scanning line substantially with a scan making positions of receive beams move so that at least one of the positions of the receive beams overlaps, the receive beams being arranged so as to receive each reflected wave from different scanning lines respectively.

17. The ultrasonic diagnostic method according to claim 11, wherein the addition step obtains the second image signal of which speckle noise is reduced by performing a weighted addition to a new image signal of a new generated frame and a result value of another weighted addition to past image signals corresponding to at least two different past frames ,and
wherein the past image signals include at least one of the first image signals and the second image signal.

18. The ultrasonic diagnostic method according to claim 11, wherein the transmitting step transmits the ultrasonic waves having a random wave surface to the subject.

19. The ultrasonic diagnostic method according to claim 11, wherein the transmitting step transmits the ultrasonic waves to the scanning lines so that phases of the wave surfaces temporally change and each shape of the wave surfaces temporally changes.

* * * * *